Figure 1:
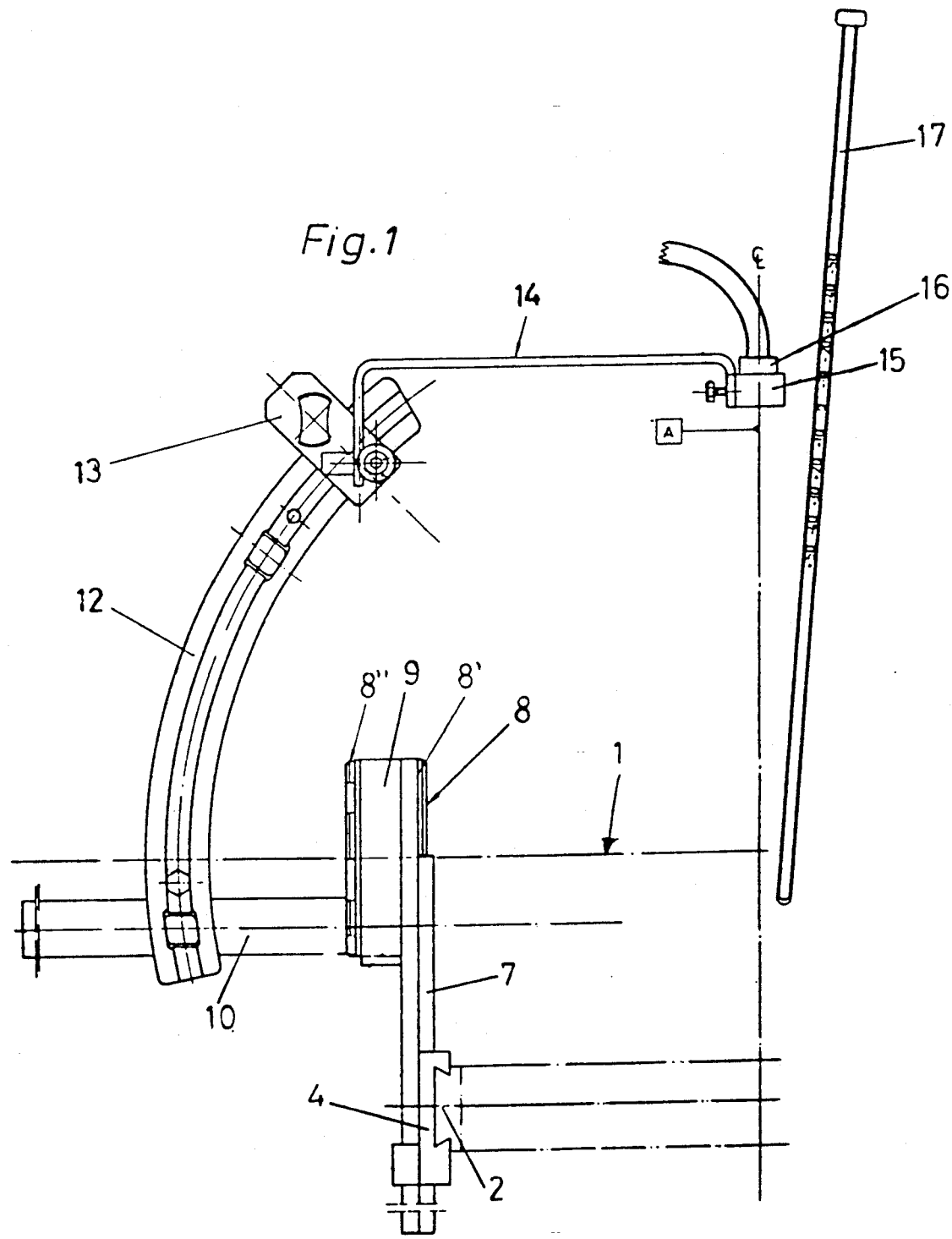

United States Patent [19]
Sundqvist

[11] Patent Number: 5,116,344
[45] Date of Patent: May 26, 1992

[54] APPARATUS FOR MARKING AN OPERATING SITE

[75] Inventor: Hans Sundqvist, Vikingstad, Sweden

[73] Assignee: Elekta Instrument AB, Stockholm, Sweden

[21] Appl. No.: 751,585

[22] Filed: Aug. 22, 1991

Related U.S. Application Data

[63] Continuation of Ser. No. 288,039, filed as PCT/SE88/00214, Apr. 27, 1988, abandoned.

[30] Foreign Application Priority Data

Apr. 27, 1987 [SE] Sweden ................. 8701719

[51] Int. Cl.⁵ .............................................. A61B 19/00
[52] U.S. Cl. ................................................. 606/130
[58] Field of Search ............... 606/130; 128/395-395, 128/630

[56] References Cited

U.S. PATENT DOCUMENTS

| | | | |
|---|---|---|---|
| 3,073,310 | 1/1963 | Mocarski | 606/130 |
| 4,215,694 | 8/1980 | Isakov et al. | 128/303.1 |
| 4,350,159 | 9/1982 | Gouda | 606/130 |
| 4,386,602 | 6/1983 | Sheldon et al. | 606/130 |
| 4,454,882 | 6/1984 | Takano | 128/395 |
| 4,592,352 | 6/1986 | Patil | 128/303 B |
| 4,638,798 | 1/1987 | Sheldon et al. | 606/130 |
| 4,638,801 | 1/1987 | Daly et al. | 128/303.1 |
| 4,651,732 | 3/1987 | Frederick | 128/303 R |

FOREIGN PATENT DOCUMENTS

| | | | |
|---|---|---|---|
| 2139433 | 2/1973 | Fed. Rep. of Germany . | |
| 2384481 | 11/1979 | France | 606/130 |

OTHER PUBLICATIONS

Advertisement, 1989 Elekta Instruments, Inc.
"Leksell Stereotactic System", 1984, pp. 2-19.

Primary Examiner—C. Fred Rosenbaum
Assistant Examiner—William Lewis
Attorney, Agent, or Firm—Shapiro and Shapiro

[57] ABSTRACT

Apparatus for marking a predetermined position of a target for surgical treatment within a patient's brain, comprises a frame for fixedly embracing the patient's skull and having at one side thereof a side-piece provided with a guide extending along a first line, a first support member mounted to the guide for adjustment along the first line and along a second line perpendicular to the first line, a rotatable member supported on the first support member for rotation about a third line perpendicular to the first and second lines, a second support member spaced from the third line and including an arm having a first end attached to the rotatable member and extending longitudinally parallel to the third line in a direction away from a side of the frame opposite the aforementioned one side, the arm thus being adjustable about the third line by rotation of the rotatable member, an arcuate support member mounted to the arm for adjustment along the third line and for adjustment transversely of the arm along an arcuate path defined by the arc of the arcuate support member, and a laser light source mounted to the arcuate support member for aiming a laser beam into the patient's skull directly at the position of the target to provide guiding beam illumination of intervening tissue on a surgical path to the target as the surgeon proceeds to the target along the path, and to mark the target when reached by the surgeon.

10 Claims, 4 Drawing Sheets

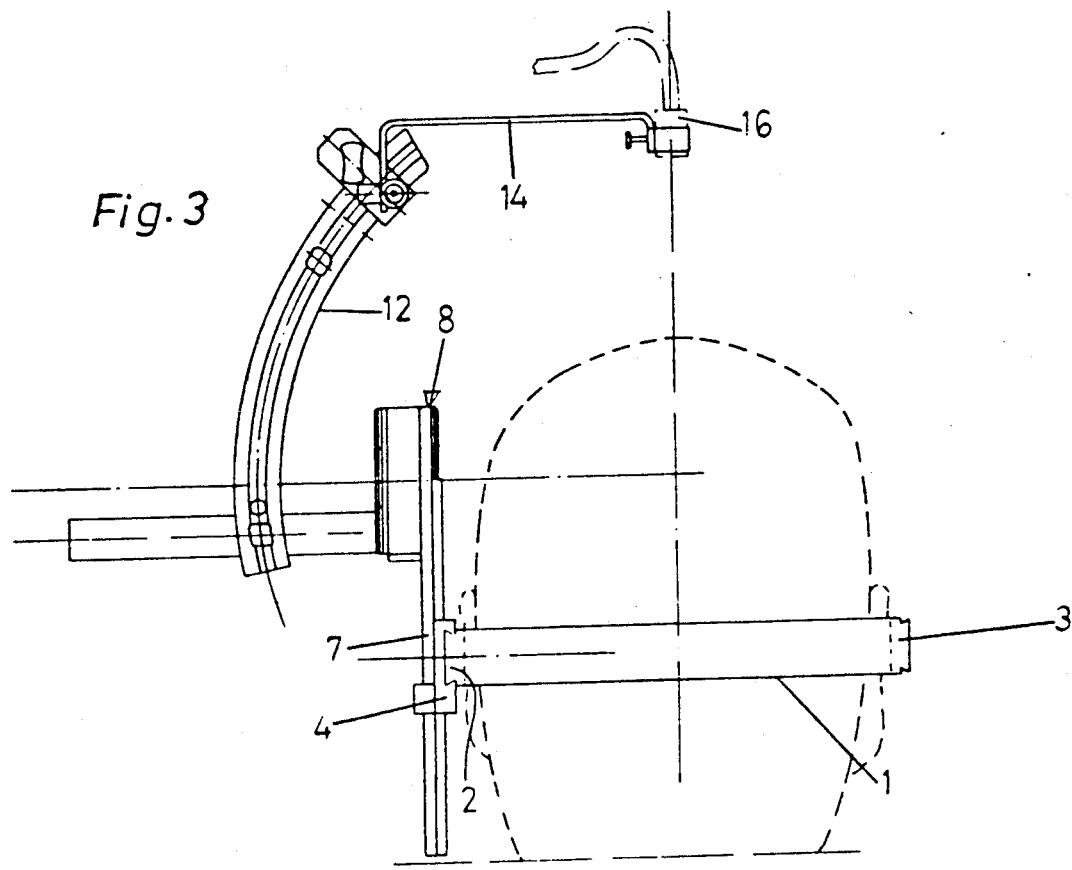
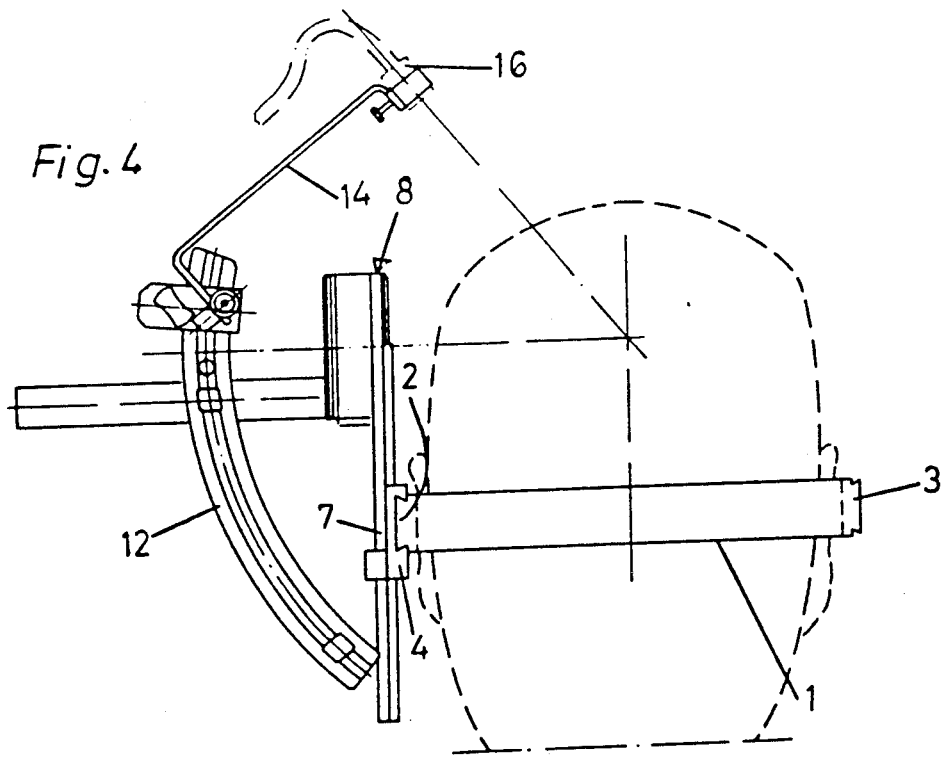

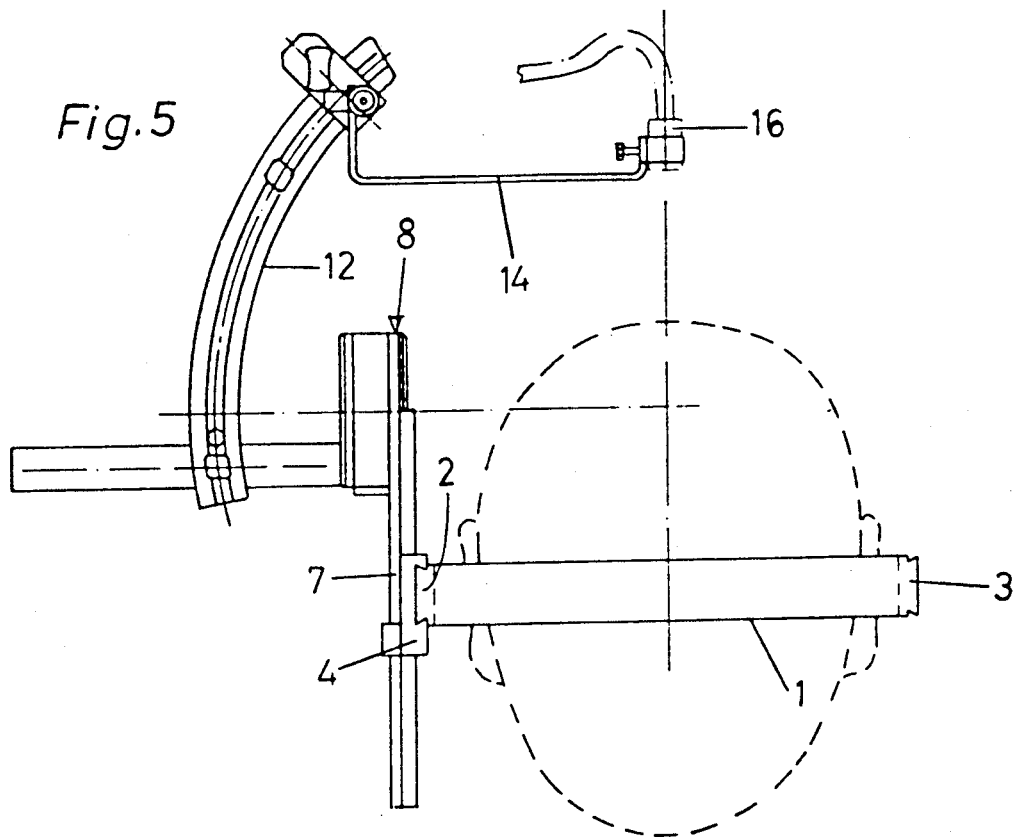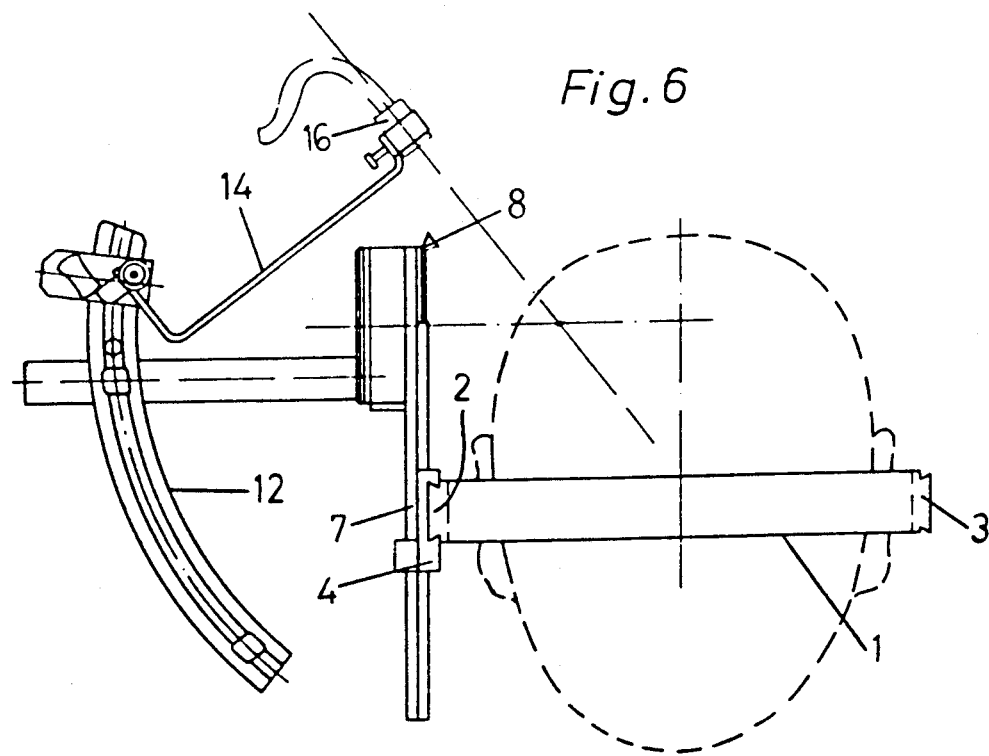

APPARATUS FOR MARKING AN OPERATING SITE

This is a continuation of application Ser. No. 288,039 filed as PCT/SE88/00214, Apr. 27, 1988, now abandoned.

The present invention relates to an apparatus for accurately defining to the surgeon, particularly in brain surgery, but also in other types of surgery, the target or operating site.

In microsurgery, as well as in surgery by scalpel and surgical laser, the surgeon must frequently work more or less by instinct on the basis of known measured values, for example the depth from the skull bone to the tissue portion to be treated and the position of such tissue portion relative to known starting points. Use is also made of a cannula, as a sighting aid, which is inserted towards the target and makes it easier for the surgeon to reach the target. The known methods must be regarded as unreliable, especially for surgery deep down and when the target, i.e. the tissue portion to be treated, is of small extent. There is thus a risk that the surgeon will fail to reach the correct site and/or be forced to perform unnecessary penetration of intervening tissue.

The object of this invention is to provide an apparatus for defining the position of an operating site.

The characteristic features of the apparatus according to the invention are stated in the claims.

The invention is based on the established fact that NMR, CT and/or X-ray equipment makes it possible to define with great accuracy the position of deep-seated tissue portions in the skull or in some other part of the body. The position can be defined by coordinates by means of a stereotactic instrument attached to the patient's head.

The invention allows the surgeon to be guided by safe and yet uncomplicated assessments of distance and depth, straight to the tissue portion to be treated.

Figure 2:
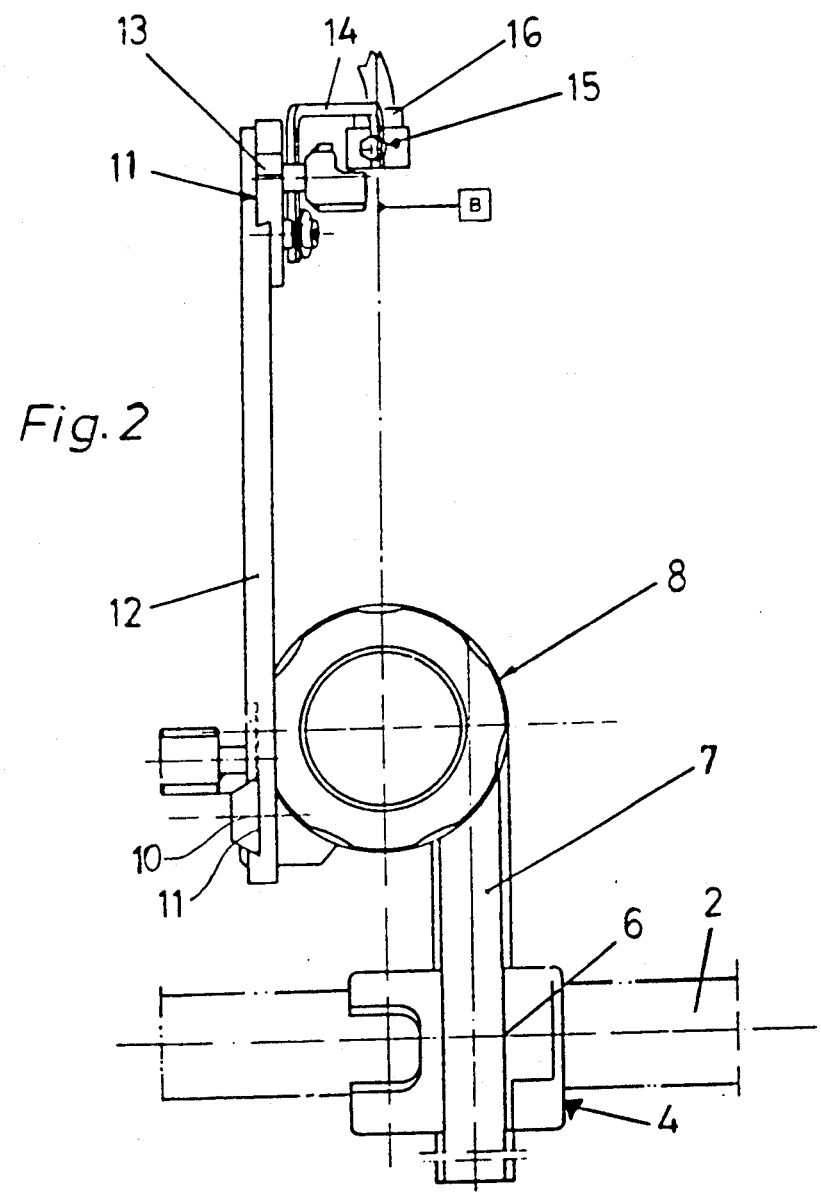

The invention will be described in greater detail below, reference being had to the accompanying drawings in which FIG. 1 is a front view of the apparatus according to the invention, FIG. 2 is a side view thereof, and FIGS. 3-6 illustrate various settings.

It is here assumed that the area to be treated (the target) has been determined by computer tomography, X-ray or NMR technique, whereby highly accurate data as to the location of the target have been obtained, and that an appropriate stereotactic instrument has been used for determining the target coordinates.

A frame which is designated 1 in the drawings, and which is dovetailed along at least two sides 2, 3 to provide guide means, is attached to the patient's head in a stable, nondisplaceable position. Along the frame side to the left in the drawings, a cross-table designated 4 is slidable along the frame side 2. The frame sides 2 and 3 are each provided with a rule (not shown), and the cross-table 4 has corresponding reference marks. The cross-table 4 comprises a guide groove 6 for a rod 7, which is also preferably dovetailed and provided with a rule, and an annular member 8 is mounted at the upper end of the rod. The annular member comprises an inner ring 8' which has a collar and is attached to the rod 7, and an outer ring 8" having an opposing collar. The cross-table also comprises locking screws (not shown) for positioning the cross-table 4 relative to the frame side 2, and the rod 7 relative to the cross-table. The rod 7 supports, via the annular member 8, a ring 9 rotatable relative to the annular member, a rule and reference marks, as well as a means for locking the ring to the annular member, being provided as well (but, for simplicity of the drawings, not shown).

A shaft 10 is mounted on the ring assembly 9, and along said shaft, which is dovetail in cross-section, an arcuate member 12 having a plurality of transverse radial dovetail grooves 11 is slidably mounted. Along the arcuate member 12 which is also dovetailed in cross-section, a slide 13 is movable. A supporting arm 14 is settably connected with the slide 13, and the free remaining end of the supporting arm is provided with a holder 15 for a light source 16 generating an aiming laser beam.

The light source may be a laser light source with a parallel bundle of light, but can also be adapted to generate two or more converging beams which can be set to coincide at a focus defining the operating site or target.

It is also possible to use a specially designed rule 17 for measuring the depth or distance to the target, starting from the light holder 15.

On the basis of the data which have been obtained upon determining the target, i.e. the tissue portion to be treated, and which are transferred to the stereotactic instrument, the coordinates are obtained which are required for setting the light source 16, while using the frame 1 as a reference, such that the beam from the light source is directed at the treating site or target.

In surgery where surgical microscopes are used (so-called microsurgery), the surgeon proceeds down to the target along the aiming laser beam and removes tissue by a surgical laser or uses conventional tools such as a scalpel or the like. Since the surgeon can constantly follow the aiming laser beam, the operation is facilitated and interference with the surrounding tissue is minimized.

With the target accurately defined by coordinates, and with the adjustability of the light source with respect to the angle and direction of incidence, the surgeon is able to choose the position of and direction for the incision. The setting of the aiming laser beam is carried out in a completely safe manner independently of which direction or angle has been chosen for the incision.

FIGS. 3-6 illustrate different settings of the light source, and it is obvious that a variety of settings are possible. The apparatus also allows, when necessary, a different entering angle to be selected during the operation without necessitating resetting. The frame can, of course, be used to position the patient's head relative to the operating table or the like and can also be used as an attachment for surgical instruments, tools or the like.

The invention is not restricted to what has been described above and shown in the drawing, but can be modified in various ways within the scope of the appended claims.

I claim:

1. Apparatus for marking a predetermined position of a target for surgical treatment within a patient's brain, comprising frame means for non-displaceable attachment to the patient's skull and having at least one guide means extending along a first line, a first support member mounted to said guide means for adjustment along said first line and along a second line perpendicular to said first line, rotatable means supported on said first support member for rotation about a third line perpendicular to said first and second lines, a second support member extending parallel to said third line in spaced relation thereto and connected to said rotatable means for adjustment about said third line by rotation of said rotatable means, an arcuate support member mounted to said second support member for adjustment along said third line and for adjustment transversely of said second support member along an arcuate path defined by the arc of said arcuate support member, and laser light source means mounted to said arcuate support member for aiming a laser beam into the patient's skull directly at the position of the target to provide guiding beam illumination of intervening tissue on a surgical path to the target as the surgeon proceeds to the target along said path and to mark the target when reached by the surgeon.

2. Apparatus according to claim 1, wherein said laser light source means is mounted to said arcuate support member by means including a slide slidable longitudinally along the arc of said arcuate support member.

3. Apparatus according to claim 1, wherein said guide means includes a side-piece of said frame means extending longitudinally along said first line, said first support member is a rod member extending longitudinally along said second line, said rod member is coupled to said guide means by a cross-piece, and said cross-piece is connected to said rod member and to said side-piece by slidable dovetail connections extending along said second line and said first line, respectively.

4. Apparatus according to claim 3, wherein said rotatable means comprises an annular coupling mounted on an end portion of said rod member, said annular coupling includes an annular member rotatable on an axis coincident with said third line, and said second support member includes an arm attached to said rotatable annular member for movement therewith.

5. Apparatus according to claim 4, wherein said laser light source means is mounted to said arcuate support member by means including a slide slidable longitudinally along the arc of said arcuate support member.

6. Apparatus for marking a predetermined position of a target for surgical treatment within a patient's brain, comprising frame means for fixedly embracing the patient's skull and having at one side thereof a side-piece provided with guide means extending along a first line, a first support member mounted to said guide means for adjustment along said first line and along a second line perpendicular to said first line, rotatable means supported on said first support member for rotation about a third line perpendicular to said first and second lines, a second support member spaced from said third line and including an arm having a first end attached to said rotatable means and extending longitudinally parallel to said third line in a direction away from a side of said frame means opposite said one side, said arm thus being adjustable about said third line by rotation of said rotatable means, an arcuate support member mounted to said arm for adjustment along said third line and for adjustment transversely of said arm along an arcuate path defined by the arc of said arcuate support member, and laser light source means mounted to said arcuate support member for aiming a laser beam into the patient's skull directly at the position of the target to provide guiding beam illumination of intervening tissue on a surgical path to the target as the surgeon proceeds to the target along said path, and to mark the target when reached by the surgeon.

7. Apparatus according to claim 6, wherein said laser light source means is mounted to said arcuate support member by means including a slide slidable longitudinally along the arc of said arcuate support member.

8. Apparatus according to claim 6, wherein said first support member is a rod member extending longitudinally along said second line, said rod member is coupled to said guide means by a cross-piece, and said cross-piece is connected to said rod member and to said side-piece by slidable dovetail connections extending along said second line and said first line, respectively.

9. Apparatus according to claim 8, wherein said rotatable means comprises an annular coupling mounted on an end portion of said rod member, said annular coupling includes an annular member rotatable on an axis coincident with said third line, and said first end of said arm is fixedly attached to said rotatable annular member.

10. Apparatus according to claim 9, wherein said laser light source means is mounted to said arcuate support member by means including a slide slidable longitudinally along the arc of said arcuate support member.

* * * * *